United States Patent [19]

Walters et al.

[11] Patent Number: 4,851,214

[45] Date of Patent: Jul. 25, 1989

[54] DEODORANTS CONTAINING N-SOYA-N-ETHYL MORPHOLINIUM ETHOSULFATE

[75] Inventors: Peter P. Walters, Claymont; Ronald I. Davis, Wilmington, both of Del.

[73] Assignee: ICI Americas Inc., Wilmington, Del.

[21] Appl. No.: 241,425

[22] Filed: Sep. 7, 1988

[51] Int. Cl.$^4$ .................. A61K 7/035; A61K 7/06; A61K 7/32; A61K 9/12

[52] U.S. Cl. .................. 424/65; 424/DIG. 5; 424/47; 424/66; 424/68; 424/69; 424/70; 424/71; 424/72; 514/944

[58] Field of Search ................................ 424/65

[56] References Cited

U.S. PATENT DOCUMENTS

| | | | |
|---|---|---|---|
| 2,417,992 | 3/1947 | Niederl et al. | 260/247 |
| 2,719,129 | 9/1955 | Richardson et al. | 252/305 |
| 2,820,719 | 1/1958 | Truslev et al. | 117/55 |
| 2,828,306 | 3/1958 | Griebsch et al. | 260/239.5 |
| 2,852,434 | 9/1958 | Taylor | 167/90 |
| 3,044,962 | 7/1962 | Brunt et al. | 252/110 |
| 3,198,251 | 8/1965 | Shore et al. | 167/22 |
| 3,287,214 | 7/1964 | Taylor et al. | 167/39 |
| 3,526,473 | 9/1970 | Burgett et al. | 8/94.12 |
| 4,110,430 | 8/1978 | Hopp et al. | 424/65 |
| 4,202,882 | 5/1980 | Schwartz et al. | 424/76 |
| 4,304,675 | 12/1981 | Corey et al. | 252/8.6 |

FOREIGN PATENT DOCUMENTS

| | | |
|---|---|---|
| 34126 | 1/1981 | European Pat. Off. |
| 50-69241 | 6/1975 | Japan |

OTHER PUBLICATIONS

Chem. Abstract: 84:79739p, Jap. Pat. 75 69241 (1976).
Chem. Abstract: 52:10507i (1958), Powers et al.

*Primary Examiner*—Dale R. Ore

[57] ABSTRACT

Personal malodors due to the chemical or bacterial action occurring on the skin or hair are inhibited by applying formulations containing N-soya-N-ethyl morpholinium ethosulfate.

4 Claims, No Drawings

DEODORANTS CONTAINING N-SOYA-N-ETHYL MORPHOLINIUM ETHOSULFATE

The present invention is directed to formulations containing N-soya-N-ethyl morpholinium ethosulfate (soyaethyl morpholinium ethosulfate) which are useful in controlling odor. There are many sources and types of malodors. It is known that body odor is primarily caused by the bacterial decomposition of lipids or proteinaceous matter secreted by the apocrine glands. Malodorous by-products such as low molecular weight fatty acids, mercaptans, amines, indoles, ammonia and hydrogen sulfide are produced.

Some cosmetic products like home permanents or depilatories generate malodors which are primarily ammonia and mercaptans.

Unpleasant odors associated with food or food processing include cabbage or onion odor. Odors like tobacco or mildew may be an undesirable aspect of indoor environments. Animals are another source of malodors.

Regardless of the source, malodors are generally low molecular weight organic molecules which are volatile. Soyaethyl morpholinium ethosulfate functions as a complexing agent for these molecules and reduces their vapor pressure. Ideally, an equimolar complex is formed between soyaethyl morpholinium ethosulfate and the malodor.

Soyaethyl morpholinium ethosulfate can be formulated into various product types, e.g., solid sticks, powders, creams, lotions and aerosols. Potential applications include solid underarm deodorants, antiperspirants or air fresheners, foot or body powders, animal care products, laundry detergents, hair care lotions and aerosol underarm deodorants or space deodorizers. In all cases, the active ingredient is a particular N-ethyl morpholinium ethosulfate derivative made from doubly distilled soya amines containing a high concentration of linoleic amine. This invention is also directed to a method for deodorizing human skin and hair by placing formulations of the invention in intimate contact therewith.

The morpholinium alkyl sulfates have been known for some time and can be made according to the process descriptions outlined in U.S. Pat. No. 2,417,992 and U.S. Pat. No. 2,852,434. In general, the morpholinium ethosulfate employed in the formulations is derived from a specific blend of Soya alkyl amines which is doubly distilled and has an initial boiling point of about 275° C. at 760 mmHg pressure, a melting point of 29° C., a specific gravity of 0.810 at 38° C. and an average molecular weight of 268. This blend contains 5-10 percent by weight n-hexadecylamine; 5-10 percent by weight n-octadecylamine; 12-17 percent by weight n-octadecenylamine (oleic); 58-62 percent by weight n-octadecedienylamine (linoleic) and 3-6 percent by weight n-octadecatrienyl amine (linoleinic) and less than 2 percent by weight disoya alkyl amines. This blend is reacted with an excess of technical dichloroethylether in the presence of an aqueous solution of sodium carbonate in sufficient excess to neutralize the liberated hydrochloric acid generated in the reaction. The reaction product is washed with hot water and the water separated out and discarded. The N-soya morpholine is stripped of water and excess dichloroethylether under vacuum then cooled and filtered to remove any insoluble material. The purified N-soya morpholine is then reacted with a stoichiometric amount of technical diethyl sulfate at temperatures at around 105°-115° C. to form N-soya N-ethyl morpholinium ethosulfate. Water is added until a concentration of 30-40 percent is obtained and a pH is adjusted to 7.5 by the addition of sodium carbonate.

The aqueous solution of the morpholinium ethosulfate described above can be adsorbed on an innocuous pharamaceutically acceptable particular to form a powder or combined with thickening agents to form a rigid stick. The morpholinium ethosulfate is combined in sufficient concentration to provide the desired odor-inhibiting effect when applied to the skin surface in the prescribed concentrations. For most purposes, effective concentrations of the morpholinium ethosulfate in the formulation may range from 0.1-0.9 percent by weight based on the total formulation. Normally, deodorant sticks, foot powders and hair conditioners contain from 0.2-0.4 percent by weight.

In the formulation of foot powders and dusting powders, the particulate substrate is selected from talc, cornstarch, titania as incorporated therewith from 0.1-0.5 percent of the morpholinium ethosulfate. The foot powder may contain other innocuous ingredients or medicaments such as perfume, coloring agents, germicides and fungicides.

Deodorant sticks are made by amending aqueous alcohol solutions containing the morpholinium ethosulfate with thickening agents such as sodium stearate and the like. Such formulations may contain perfume, medications, coloring agents, fungicides, germicides and drying agents, as well as other preservatives.

Hair care formulations include permanent wave lotions, neutralizing lotion, clear hair conditioning lotions, cream hair rinses, hair conditioning gels and styling conditioning mousses. Personal care products also include depilatories containing the morpholinium ethosulfate. When employed in such formulations, it is included to offset the mercaptan odor accompanying the chemical treatment of hair in the permanent wave process.

Aerosol formulas typically are hydroalcoholic solutions containing biocides and/or fragrances. Morpholinium ethosulfate can be used at levels ranging from 0.01 to 1.0 percent by weight.

In laundry products, 0.1 to 0.5 percent by weight morpholinium ethosulfate can be used in either the wash or rinse cycle along with traditional detergents or softeners.

A typical animal products application would be a solid kitty litter product containing 0.1 to 0.5 percent by weight morpholinium ethosulfate.

The practice of the invention may be better understood with reference to the following preparations and formulations wherein all proportions expressed are by weight unless otherwise specified.

PREPARATION 1

Preparation of Soyaethyl Morpholinium Ethosulfate (35 Percent Active Aqueous Solution)

Commercially available, doubly distilled soyaalkyl amines (Armeen ® SD) containing 15-20 percent by weight of a blend of n-hexadecylamine and n-octadecylamine; 15 percent n-octadecenylamine; 60 percent n-octadecadienylamine; and 5 percent n-octadecatrienylamine containing less than 2 percent by weight disoya alkyl amines is reacted with a 10 percent molar excess of technical dichloroethylether in the presence of at least 1 molar quantity of sodium carbonate sufficient to neutralize all liberated hydrochloric acid. This reaction product is washed with hot water and separated by decantation. The oil layer is stripped of water and excess dichloroethylether under vacuum, then cooled and filtered to remove any insoluble material. The product is analyzed for water content, hydrochloric acid equivalent and tertiary amine. This product containing less than 0.15 percent moisture is tested for the tertiary amine content as determined by the hydrochloric acid equivalent. A stoichiometric amount equivalent to the hydrochloric acid equivalent of diethylsulfate is added to the n-soyamorpholine product at a temperature of 100°-115° C. to form the N-soya N-ethylmorpoline ethosulfate. Water is added until a concentration of 35 percent is obtained and the pH is adjusted to 7.5 with caustic soda. Activated carbon is added and the solution is filtered, hot cooled and adjusted to a concentration of 35 percent.

EXAMPLE 1

In order to show the efficacy of Preparation 1, deodorant sticks were prepared containing various concentrations. These formulas were tested on human subjects. A control stick contained 0.25% 2,4,4'-Trichloro-2'-hydroxydiphenylether. Sticks were also tested containing both Preparation 1 and 2,4,4'-Trichloro-2'hydroxydiphenylether. The base formula for this stick was:

X % Preparation 1
78% ethy alcohol
10% water
6% propylene glycol
6% sodium stearate
Preparation:
Heat with stirring until sodium stearate dissolves. Remove heat and replace any alcohol lost during the process. Immediately pour into molds.

Test No. 1

Formulas contained 0.25% Preparation 1, 0.25% or 2,4,4'-Trichloro-2'-hydroxydiphenylether or no active. Product was applied for 3 consecutive days after an appropriate conditioning period. Odor evaluations were made 12 hours after the final two treatments.

| Formula Active | % Odor Reduction | |
|---|---|---|
| | 24 hrs. | 36 hrs. |
| 0.25% Preparation 1 | 71 | 48 |
| 0.25 2,4,4'-Trichloro-2'-hydroxydiphenylether | 67 | 52 |

Test No. 2

Formulas contained a combination of 0.15% Preparation 1 plus 0.10% 2,4,4'-Trichloro-2'-hydroxydiphenylether, 0.25% 2,4,4'-Tricholor-2'-hydroxydiphenylether or no active. Product was also applied for 3 consecutive days. Odor evaluations were made 24 hours after the final two treatments.

| Formula Active | % Odor Reduction | |
|---|---|---|
| | 48 hrs. | 72 hrs. |
| 0.15% Preparation 1 0.10% 2,4,4'-Trichloro-2'-hydroxydiphenylether | 48 | 32 |
| 0.25% 2,4,4'-Trichloro-2'-hydroxydiphenylether | 27 | 30 |

The activity of Preparation 1 is most significant during the first 24 hours of use because it acts immediately to deodorize the malodors resulting from perspiration. After this time, the antimicrobial activity of the formula attains its ultimate potential.

EXAMPLE 2

Deodorant Stick

| | % Weight |
|---|---|
| Ethyl alcohol | 77.90 |
| Water | 9.57 |
| Propylene glycol | 6.00 |
| Sodium stearate | 6.00 |
| Preparation 1 | 0.43 |
| 2,4,4'-Trichloro-2'-hydroxydiphenylether | 0.10 |
| | 100.0 |

Preparation

Heat with stirring until sodium stearate dissolves. Remove heat and replace any alcohol lost during process. Immediately pour into molds.

EXAMPLE 3

Antiperspirant/Deodorant Stick

| | % Weight |
|---|---|
| A | |
| Volatile silicone, Dow Corning ® 344 Fluid (Dow Corning Corp.) | 51.1 |
| Stearyl alcohol | 23.0 |
| Hydrogenated castor oil | 3.0 |
| BRIJ ® 78, Steareth-20 (ICI Speciality Chemicals) | 1.0 |
| Preparation 1 | 1.4 |
| B | |
| Aluminum zirconium trichlorohydrate, Rezal ™ 36 GP (Reheis Chemical Co.) | 20.0 |
| Fumed silica, Cab-O-Sil ® M5 (Cabot Corp.) | 0.5 |
| | 100.0 |

Preparation

Heat (A) slowly with stirring until fluid and homogenous. Add (B) and continue stirring for 5 minutes. Allow to cool to 55° C. and pour in stick casings.

EXAMPLE 4

Foot Powder Formula 99.9–99.5% Talc and/or cornstarch
0.1–0.5% Soyaethyl morpholinium enthosulfate Preparation Prepare a 10% solution of soyaethyl morpholinium ethosulfate in ethyl alcohol. Spray this solution onto the powder base with thorough mixing. Heat gently or air dry to evaporate solvent.

EXAMPLE 5

Clear Hair Conditioner Lotion

|  | % Weight |
|---|---|
| A | |
| Hydroxyethyl cellulose Natrosol 250 HR (Hercules Incorporated), 3% solution | 40.0 |
| B | |
| Preparation 1 | 1.4 |
| Water | 58.6 |
|  | 100.0 |

Preparation

Prepare (A) in advance by dispersing hydroxyethyl cellulose in water to yield a 3% solution. Prepare solution (B). Add (B) to (A) with stirring until homogenous.

Preparation 1 can also be used effectively in an opacified "cream rinse" lotion like the one shown below.

EXAMPLE 6

Cream Hair Rinse

|  | % Weight |
|---|---|
| Cetyl alcohol | 1.5 |
| BRIJ ® 721, Steareth-21 (ICI Specialty Chemicals) | 1.0 |
| Preparation 1 | 1.4 |
| Water | 96.1 |
|  | 100.0 |

Preparation

Heat to 70° C. with stirring until uniform. Cool with stirring and add make-up water at 50° C.

Preparation 1 in a surfactant gel is a good hair dressing. The formula is a clear (microemulsion), "ringing" gel.

EXAMPLE 7

Hair Conditioning Gel

|  | % Weight |
|---|---|
| A | |
| Mineral Oil | 11.0 |
| ARLASOLVE ® 200, Isoceteth-20 (ICI Speciality Chemicals) | 20.0 |
| BRIJ ® 93, Oleth-2 (ICI Speciality Chemicals) | 6.0 |
| B | |
| Water | 49.6 |
| Propylene glycol | 5.0 |
| SORBO ® Sorbitol Solution ICI Speciality Chemicals) | 7.0 |
| Preparation 1 | 1.4 |
|  | 100.0 |

Preparation

Heat (A) and (B) to 90° C. Add (B) to (A) with gentle stirring. Cool to 80° C. and add make-up water. Stir until uniform and pour while still fluid.

Preparation 1 styling/conditioning mousse is shown in Example 8. It includes Preparation 1 as a conditioner, a silicone copolymer to improve wet combing and polymeric resin for setting.

EXAMPLE 8

Styling/Conditioning Mousse

|  | % Weight |
|---|---|
| A | |
| Preparation 1 | 1.4 |
| BRIJ ® 721 Steareth-21 (ICI Speciality Chemicals) | 0.5 |
| Dow Coring 929 Emulsion, Amodimethicone (and) Nonoxynol-10 (and) Tallowtrimonium chloride | 0.1 |
| Water | 78.0 |
| B | |
| Gaffix VC-713, Vinylcaprolactam/ PVP/Dimethylaminoethyl methacrylate copolymer (GAF) | 5.0 |
| SD Alcohol 40 | 10.0 |
| C | |
| Hydrocarbon Propellant A-46 | 5.0 |
|  | 100.0 |

Preparation

Heat (A) to 60° C. with stirring until uniform. Cool to 40° C. Add (A) to (B) with stirring. Pack in suitable aerosol containers and pressurize with (C) at room temperature.

EXAMPLE 9

Home Permanent Formulations

One obvious applications for soyaethyl morpholinium ethosulfate is in home permanents as a deodorizer/conditioner. The following example is a basic formula without optical ingredients like opacifiers or thickeners.

Permanent Wave Lotion

|  | %, Weight |
|---|---|
| A | |
| Soyaethyl morpholinium ethosulfate | 0.5 |
| BRIJ ® 35 SP, Laureth-23 (ICI Speciality Chemicals) | 2.0 |
| Water | 81.0 |
| B | |
| Ethanolamine | 9.5 |
| C | |
| Thioglycolic acid | 7.0 |
|  | 100.0 |

Preparation

Mix (A) with gentle heat if necessary until uniform. Add (B). Add (C). Adjust pH to 9.0–9.5 with additional ethanolamine or thioglycolic acid.

Neutralizing Lotion

|  | %, Weight |
|---|---|
| A | |
| Soyaethyl morpholinium ethosulfate | 0.5 |
| BRIJ ® 35 SP | 2.0 |
| Water | 93.2 |
| Stabilizer | q.s. |

-continued

| | %, Weight |
|---|---|
| B | |
| Hydrogen peroxide, 35% | 4.3 |
| C | |
| Phosphoric acid | q.s. |
| | 100.0 |

Preparation

Mix (A) until uniform. Add (B) at 25° C. Adjust pH to 4.5–5.0 with (C). Optional stabilizers may include sequestrants or antioxidants.

Tresses of human hair were treated with home permanent formulas containing 0.5% soyaethyl morpholinium ethosulfate in both wave lotion and neutralizing lotion. Control treatments were also carried out using perm solutions without soyaethyl morpholinium ethosulfate. The post-treatment odor of dry hair was reduced when soyaethyl morpholinium ethosulfate was present in either or both solutions.

EXAMPLE 10

Cat Litter Formula 99.9–99.5% Clay or other adsorbent 0.1–0.5% Soyaethyl morpholinium ethosulfate Preparation Prepare a 10% solution of soyaethyl morpholinium ethosulfate in ethyl alcohol. Spray this solution onto the adsorbent substrate with thorough mixing. Heat gently or air dry to evaporate solvent.

What is claimed is:

1. A method for inhibiting malodors due to bacterial or chemical action occurring on skin or hair which comprises coating or dusting the area to be inhibited with a formulation containing an effective amount of N-soya-ethylmorpholinium ethosulfate derived from doubly distilled soya amine blend containing from 15–20% combined weight of N-hexadecylamine and n-octadecylamine; 15% octadecenylamine; 60% octadecylidienylamine; and 5% octadecyltrienylamine.

2. A method of claim 1 wherein said formulations contains from 0.1–0.4% by weight of N-soya N-ethyl morpholinium ethosulfate.

3. A method of claim 1 wherein said formulation is in the form of a hair lotion, antiperspirant, stick deodorant or dusting powder.

4. A method of claim 1 wherein said soya amine blend consists essentially of doubly distilled amine blend having an initial boiling point of 275° C. and a molecular weight of 268.

* * * * *